(12) United States Patent
Lenssen et al.

(10) Patent No.: US 10,810,855 B2
(45) Date of Patent: Oct. 20, 2020

(54) SYSTEM AND METHOD FOR MONITORING ACTIVITIES OF DAILY LIVING OF A PERSON

(71) Applicant: SIGNIFY HOLDING B.V., Eindhoven (NL)

(72) Inventors: Kars-Michiel Hurbert Lenssen, Veldhoven (NL); Murtaza Bulut, Eindhoven (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 0 days.

(21) Appl. No.: 16/343,845

(22) PCT Filed: Oct. 17, 2017

(86) PCT No.: PCT/EP2017/076465
§ 371 (c)(1),
(2) Date: Apr. 22, 2019

(87) PCT Pub. No.: WO2018/073241
PCT Pub. Date: Apr. 26, 2018

(65) Prior Publication Data
US 2019/0244508 A1      Aug. 8, 2019

(30) Foreign Application Priority Data

Oct. 20, 2016   (EP) .................................... 16194723

(51) Int. Cl.
*G08B 23/00*        (2006.01)
*G08B 21/04*        (2006.01)
(Continued)

(52) U.S. Cl.
CPC ........ *G08B 21/0423* (2013.01); *A61B 5/0002* (2013.01); *A61B 5/0022* (2013.01);
(Continued)

(58) Field of Classification Search
CPC . G08B 21/0423; A61B 5/0022; A61B 5/6889; A61B 5/7282; A61B 5/1118; A61B 2503/08
See application file for complete search history.

(56) References Cited

U.S. PATENT DOCUMENTS

2004/0030531 A1    2/2004 Miller et al.
2008/0001735 A1    1/2008 Tran
(Continued)

FOREIGN PATENT DOCUMENTS

EP            0558975 B1     12/1997
KR          2014080585 A      7/2014
(Continued)

*Primary Examiner* — Toan N Pham
(74) *Attorney, Agent, or Firm* — Meenakshy Chakravorty (57) ABSTRACT

Presented is a system and method for monitoring activities of daily living, ADLs, of a person within an environment containing an object that is controllable by the person via a control system. The system comprises a data collection unit adapted to obtain control data from the control system, the control data being based on one or more control signals generated by the control system for controlling the object. A data analysis unit is 5 adapted to determine an ADL event of the person based on the obtained control data.

14 Claims, 4 Drawing Sheets

(51) Int. Cl.
*A61B 5/00* (2006.01)
*A61B 5/11* (2006.01)
*G06F 19/00* (2018.01)

(52) U.S. Cl.
CPC .......... *A61B 5/1118* (2013.01); *A61B 5/6889* (2013.01); *A61B 5/7282* (2013.01); *G06F 19/3418* (2013.01); *G08B 21/0484* (2013.01); *A61B 5/1117* (2013.01); *A61B 2503/08* (2013.01)

(56) References Cited

U.S. PATENT DOCUMENTS

| | | | |
|---|---|---|---|
| 2016/0027278 A1* | 1/2016 | McIntosh | G08B 21/0423 715/741 |
| 2018/0254096 A1* | 9/2018 | Karunanithi | A61B 5/746 |
| 2019/0244508 A1* | 8/2019 | Lenssen | A61B 5/0002 |

FOREIGN PATENT DOCUMENTS

| | | |
|---|---|---|
| WO | 2006109981 A1 | 10/2006 |
| WO | 2015185704 A1 | 12/2015 |
| WO | 2016113162 A1 | 7/2016 |

\* cited by examiner

SYSTEM AND METHOD FOR MONITORING ACTIVITIES OF DAILY LIVING OF A PERSON

CROSS-REFERENCE TO PRIOR APPLICATIONS

This application is the U.S. National Phase application under 35 U.S.C. § 371 of International Application No. PCT/EP2017/076465, filed on Oct. 17, 2017 which claims the benefit of European Patent Application No. 16194723.9, filed on Oct. 20, 2016. These applications are hereby incorporated by reference herein.

FIELD OF THE INVENTION

This invention relates to a system and method for monitoring activities of daily living of a person.

BACKGROUND OF THE INVENTION

Functional assessment or monitoring of a person's health status, physical abilities, mental abilities, or recuperation after injury, hospitalization and treatment is of primary concern in most branches of medicine, including geriatrics, rehabilitation and physical therapy, neurology and orthopedics, nursing and elder care.

Investigations have found that an individual's functional ability is actually environment-specific, since function increases when subjects are in familiar surroundings due to reduced confusion. Also, one-time assessment of function does not allow for assessment of variability of functional performance over the course of a day or several days, nor does it allow for assessment of change which is important in determining the adequacy of certain clinical services and treatments (such as rehabilitation) following functional loss.

A consensus therefore exists that it is preferable to assess or monitor independent functioning of a person at their home or within familiar surroundings.

A level of independent function is commonly indicated by the quality in which Activities of Daily Living (ADLs) are performed. ADLs refer to the most common activities that people perform during a day. Therefore, a reduced quality in the ADLs can be an indicator for care needed. For example, an anomaly in the regular performance of one or more ADLs can serve as warning for special attention.

Devices and systems have been developed to monitor the ADLs of individuals as they live independently in their own home or within familiar surroundings. For example, one such known system for detecting activities of daily living of a person comprises three main components: (i) a sensor system that collects information about the person's activities and behaviors; (ii) an intelligence (or information processing) system that interprets the sensor signals for determination of ADL behavior; and (iii) a user interface system that enables care givers to inspect the interpreted (processed) information. The intelligence system typically makes use of computational techniques known in the art as artificial intelligence. The system may be supported by conventional technologies for data collection, transmission, and storage.

A system and method for monitoring activities of daily living, ADLs, of a person within an environment is described in WO 2016/113162 A1. The disclosed system comprises an ADL inference unit adapted to receive a sensor output signal representative of a detected value of a property of at least one of the person and the environment, and to generate an inferred ADL output signal representative of the inferred ADL of the person. A monitor unit is adapted to generate a monitor signal dependent on at least one of the received sensor output signal and the inferred ADL output signal. Similar systems and methods are disclosed in US 2008/001735 A1, EP 0 558 975 A1 and US 2004/030531 A1.

In practice, however, a major difficulty is encountered by the wide range of variations that can happen in actual care cases. Since there are so many possible circumstances, situations and contexts that can occur in daily life, it is common to employ numerous sensors in an attempt to capture enough information about a person's activities to enable identification of specific activities. This, however, typically increases costs and may therefore be undesirable.

Also, a monitored person's physical and/or mental abilities may vary (e.g. decline or reduce) over time. As a result, it can be difficult to determine when some form of assistance, help of supervision may be needed.

SUMMARY OF THE INVENTION

The invention is defined by the claims.

According to a first aspect of the invention, there is provided a system for monitoring activities of daily living, ADLs, of a person within an environment, the environment containing an object controllable by the person via a control system, the system comprising: a data collection unit adapted to obtain control data from the control system, the control data being based on one or more control signals generated by the control system for controlling the object; and a data analysis unit adapted to determine an ADL event of the person based on the obtained control data.

Embodiments may be based on the insight that a system for monitoring a person may be adapted to obtain usage data directly from control signals generated by an environment control system (such as a 'smart-home' control system for example). Thus, rather than employing numerous sensors and attempting to use sensor data, proposed embodiments may use data (e.g. control data) generated by a control system. By using data directly from a control system, embodiments may determine (e.g. infer) information about an ADL of the person without relying on complex and/or expensive sensor arrangements, thus reducing costs. Also, embodiments may avoid a need to install, commission and/or maintain sensors in a monitored environment.

Thus, ADLs of a person may be inferred from usage data that is obtained from a control system used by the person to control one or more objects. For example, a 'smart-home' control system may be adapted to control lighting and/or appliances within a monitored home environment, and control data based on actual control signals generated by the smart-home control system may be analyzed so as to determine one or more ADLs of a person who uses the control system. For instance, lighting usage data may be obtained from lighting commands generated and issued by the control system, and such lighting usage data may be analyzed to infer an ADL of the person. In this way, no additional sensors and/or monitors (such a light switch monitors, or light sensors, etc.) may be required in order to determine and monitor an ADL.

By way of further explanation, ADLs concern basic activities that a person executes on a regular basis. Examples of activities of daily living include: drinking/eating; cooking; medicating; sleeping; toileting; bathing; washing, any kind of exercising such as walking, leisure activities such as reading or TV watching and many more etc.

Embodiments may thus provide information on the ADLs of a person in a non-intrusive manner (e.g. without requiring a person to wear, operate or otherwise employ a sensor). Embodiments may also provide a way to monitor an ADL (such as cooking, eating, exercising, opening doors, etc.) in a simple and easy to implement manner, without requiring new or additional sensors to be installed for example.

Some embodiments may further comprise a monitor unit adapted to determine a trend in a capability or activity of the person based on the determined ADL event and historical data relating to previously determined ADL events of the person.

Thus, there may be proposed a concept of monitoring a physical or mental capability of a person by identifying a trend in the physical or mental capability using detected or determined ADLs of the person. By using a currently sensed or determined ADL, along with one or more previously determined ADLs, a trend, change or drift of the ADL (or a property thereof) may be identified. For example, by detecting a consistent change or pattern in detected ADLs (or ADL parameter values) over time, a trend in a person's (physical or mental) capability or activity may be inferred and, from this, current and/or future care/help/assistance requirements may be determined. Thus, there may be proposed a concept of determining a trend in a person's capability or activity based on current and historical ADLs determined from control data directly obtained from a control system (and not from sensors). For instance, an inferred ADL (or value of an ADL property) of the person may be used to infer a physical or mental capability of a person, and this may be undertaken numerous times over an extended time period (such as hours, days, weeks, months or years) so as to enable monitoring of the person's physical or mental capability over time. Furthermore, detected ADL parameters values (e.g. reaction times, movement speeds, etc.) for a predetermined timeframe (e.g. a week or month) may be used to estimate a trend in a physical or mental capability of the person for a current, following and/or preceding timeframe.

A trend in the physical or mental capability of a person may therefore be inferred without employing a complex and/or expensive sensor arrangement within a monitored environment. This may help to reduce associated cost and/or complexity of an ADL monitoring system. For example, conventional ADL monitoring systems may be adapted to detect or monitor eating and drinking by employing sensors installed on a refrigerator (e.g. an open-close sensor), sensors installed in cupboards/drawers holding cutlery/food, power sensors on cooking equipment, presence sensors for detecting a user's presence in kitchen; a pressure sensor installed in a seat of a dining table, etc. Conversely, embodiments may avoid the need for multiple sensors (and complex signal processing of their respective signals) and may instead simply employ control data obtained directly from a control system that is adapted to control one or more objects in the monitored environment.

For example, a trend of declining/decreasing velocity or speed of movement of the person (as inferred from timings between particular control signals/commands issued by a lighting control system) may be used to infer and monitor the person's physical strength or speed, and may further identify a future point in time where the person's physical strength or speed declines to a point where assistance or help will be required. By way of another example, a trend of increasing reaction time of the person (as detected based on elapsed time between a prompt or signal and a response from the person) may be used to identify and monitor the person's physical or mental capability in responding to a command, and further identify a future point in time where the person's capability will reduce to a level where additional assistance or help will be required. For example, predictive analytics may be employed to try and identify (and thus prevent or avoid) undesirable or worst case outcomes. This may help to provide cost savings (e.g. in a health care system) by timely enabling intervention. Embodiments may therefore be useful for identifying future requirements of a monitored person, and this may be achieved via extrapolation of a trend determined by a proposed embodiment.

Embodiments may therefore enable for the monitoring of a person's physical or mental capability by analyzing object activity (e.g. usage of lighting, appliances, or controllable items of furniture, heating, air conditioning) based on control signal/commands issued by a control system for the object(s) and inferring a trend from detected changes in activity, such as changes in the frequency, speed, pattern, or ease of usage of the object(s).

In some embodiments, the monitor unit may be further adapted to detect an irregularity in the determined trend. For example, the monitor unit may be adapted to detect an irregularity based on a comparison of the determined trend with a threshold value. For example, this may provide the advantage that an alarm may be given if the person stays too long in the bathroom with the hot shower running indicating that for example the person has become unwell in the bathroom. By way of example, in some embodiments, the threshold value may be determined based on at least one of: one or more previously determined ADL events of the person; and one or more previously determined changes in ADL events of the person.

To detect an irregularity, the monitor unit may undertake a comparison of the determined trend with a threshold value. For example, the monitor unit may employ a data processing unit that compares the determined trend with a threshold value and then generates an alert signal if the determined trend exceeds the threshold value. The threshold may be preprogrammed and fixed, but it may be preferable to enable the threshold value to be set by a user preference. Also, the threshold value may relate to a future value, and the trend may be extrapolated for comparison of an extrapolated value with the future threshold value. This may identify when a threshold value may be exceeded in the future, for example.

In an embodiment, the monitor unit may be further adapted to calculate an estimated future value of the property based on the determined trend, and the monitor unit may be further arranged to detect an irregularity based on a comparison of the estimated future value of the property with a threshold value and to generate an alert output signal in response to the detected irregularity.

Embodiments may further comprise a user input interface adapted to receive a user input for defining or modifying one or more alert conditions, and the monitor unit may be adapted to generate an alert output signal based on the determined trend and the one or more alert conditions.

Further, the threshold may be based on previously detected ADLs (or parameter values thereof) and/or a previously determined trend in an ADL of the person. For instance, the threshold value may be determined based on at least one of: one or more previously detected values of the property; and one or more previously determined changes in values of the property. In other words, the threshold may be defined by taking account of a history of detected values and/or a history of changes in values of the property so that it can be used to identify outlying values or anomalies.

In a further embodiment of the system the data analysis unit may be further adapted to store the determined ADL of the person in an activity database. Previously determined ADLs (or values of a property of the ADLs) may therefore be stored, in a historical database for example, and then used in subsequent calculations. Furthermore, currently detected ADLs or values may be used to re-calculate or refine a previously determined trend.

Thus, the behavioral pattern of activities of the person may be stored. Shifts in this pattern may indicate that the person is in need of help. For example, the person may start forgetting to take a regular shower, and this may be inferred from a trend in a frequency of lighting command signals issued to a shower room of the monitored home by a lighting control system of the home.

The data analysis unit may be further adapted to detect an irregularity in the activity database. For example, by adding time information to the determined ADL(s), the time spent between the activities may be determined. With the time information, the frequency of the activity may be determined. For example, the frequency of the determined activity 'preparing a hot meal' may be 'once a day', or '5 times a week'. An irregularity in the activity database may then, for example, be that the time spent between the determined activities of 'preparing a hot meal' has increased. For example the average time spent may be determined using the data from the activity profile. When the time spent between two successive determined activities of 'preparing a hot meal' is larger than for example 1.5 times the average time spent this indicates an irregularity.

In a further embodiment, the data analysis unit may be further arranged to generate a warning signal in response to a detected irregularity. The irregularity may indicate that the person is in need of help. In a further example, a medical practitioner, a caregiver, a family member or close relative may be advised by the system (using the alert signal) to pay a visit to the person. In a further embodiment the warning signal may be provided to the person himself/herself. For example, the warning signal may be a feedback signal advising the person to take a certain medication.

Embodiments may be adapted to provide a generated alert or warning signal to at least one of: the person; a medical practitioner; and a caregiver.

Embodiments may further comprise a control unit adapted to generate a control signal for controlling the object based on the determined ADL event. In this way, embodiments may be adapted to provide control signals that are suitable for use by the control system, thereby enabling embodiments to modify or control operation of the control system (and thus the object(s) controlled by the control system). For example, beyond monitoring, embodiments may also control objects/devices (that are normally controlled by the control system) based on the obtained control data. This may be done directly, by generating and communicating a control signal to an object so as to control (e.g. change, modify or adapt) its operation, or done indirectly by communicating a signal to the control system so as to cause the control system to control the object in response. In this way, operation of an object (such as a light) may be adapted based on the obtained control data (e.g. to alter the lighting conditions).

By way of example, the object may comprise a lighting device or home appliance adapted to be used for the execution of an ADL. Also, the control system may be a smart-home control system adapted to control one or more operations of a light and/home application within the smart-home.

An embodiment may be further adapted to generate a display control signal for modifying a graphical element based on the determined ADL event of the person, and the system may further comprise: a display system adapted to display the graphical element in accordance with the generated display control signal. In this way, a user (such as a care giver) may have an appropriately arranged display system that can receive and display information about a determined ADL, and that person may be remotely located from the user. Embodiments may therefore enable a user to remotely monitor a person using a portable display device, such as a laptop, tablet computer, mobile phone, PDA, etc.

It will be appreciated that all or part of a system according to an embodiment may comprise one or more data processing units. For example, the data analysis unit may be implemented using a single processor which is adapted to undertake data processing in order to determine an ADL of the person (based on obtained usage data from a control system). The data analysis unit may be remotely located from the control system, and a control data representative of control signals issued by the control system may be communicated to the data analysis unit via a communication link.

The system may further comprise: a server device comprising the data analysis unit; and a client device comprising the data collection unit. Dedicated data processing means may therefore be employed for the purpose of determining an ADL of the person, thus reducing processing requirements or capabilities of other components or devices of the system.

The system may further comprise a client device, wherein the client device comprises the data analysis unit and a display system. In other words, a user (such as a care giver) may have an appropriately arranged client device (such as a laptop, tablet computer, mobile phone, PDA, etc.) which processes received control system usage data in order to determine an ADL of the person.

Thus, processing may be hosted at a different location from where the control signals are generated or issued. For example, for reasons of power efficiency (e.g. to improve battery lifetime) it might be advantageous to execute part of the processing at the control system location, thereby reducing associated costs, processing power, transmission requirements, etc.

Embodiments may also enable some of the processing load to be distributed throughout the system. For example, pre-processing may be undertaken at a control system. Alternatively, or additionally, processing could be undertaken at a communication gateway. In some embodiments, processing may be undertaken at a remote gateway or sever, thus relinquishing processing requirements from an end-user or output device. Such distribution of processing and/or hardware may allow for improved maintenance abilities (e.g. by centralizing complex or expensive hardware in a preferred location). It may also enable computational load and/or traffic to be designed or located within a networked system according to the processing capabilities available. A preferable approach may be to process control signals locally and transmit extracted control data for full processing at a remote server.

Thus, it will be understood that processing capabilities may be distributed throughout the system in different ways according to predetermined constraints and/or availability of processing resources.

According to another aspect of the invention, there is provided a method for monitoring activities of daily living, ADLs, of a person within an environment, the environment containing an object controllable by the person via a control system, the method comprising: obtaining control data from the control system, the control data being based on one or more control signals generated by the control system for controlling the object; and determining an ADL event of the person based on the obtained control data.

The non-intrusive character of the monitoring is realized by analyzing control data (e.g. usage) of a control system, rather than by sensing or surveillance by sensors.

In a further embodiment, the method may further comprise the step of: determining a trend in a capability or activity of the person based on the determined ADL event and historical data relating to previously determined ADL events of the person.

According to yet another aspect of the invention, there is provided a computer program product for monitoring activities of daily living, ADLs, of a person within an environment, the environment containing an object controllable by the person via a control system, wherein the computer program product comprises a computer-readable storage medium having computer-readable program code embodied therewith, the computer-readable program code configured to perform all of the steps of an embodiment of a method for monitoring activities of daily living, ADLs, of a person within an environment.

In an embodiment, a computer system may be provided which comprises: a computer program product according to an embodiment; and one or more processors adapted to perform a method according to an embodiment by execution of the computer-readable program code of said computer program product.

In a further aspect the invention relates to a computer-readable non-transitory storage medium comprising instructions which, when executed by a processing device, execute the steps of a method for monitoring activities of daily living, ADLs, of a person within an environment according to an embodiment.

These and other aspects of the invention will be apparent from and elucidated with reference to the embodiment(s) described hereinafter.

BRIEF DESCRIPTION OF THE DRAWINGS

Examples in accordance with aspects of the invention will now be described in detail with reference to the accompanying drawings, in which.

DETAILED DESCRIPTION OF THE EMBODIMENTS

Proposed is a concept for monitoring activities of daily living, ADLs, of a person within an environment, which may be useful for the purpose of unobtrusively monitoring the well-being of the person for example. Such persons may, for instance, include a disabled person, an elderly person, an injured person, a medical patient, etc. Elderly persons can mean persons above 50 years, above 65 years, above 70, or above 80 years old.

Illustrative embodiments may be utilized in many different types of monitoring environments, such as a hospital, ward, care home, person's home, etc. In order to provide a context for the description of elements and functionality of the illustrative embodiments, the Figures are provided hereafter as examples of how aspects of the illustrative embodiments may be implemented. It should therefore be appreciated the Figures are only examples and are not intended to assert or imply any limitation with regard to the environments, systems or methods in which aspects or embodiments of the present invention may be implemented.

It has been recognized that, in many care situations, there is a need to be informed about the ADLs a person is performing. There may also be a need to be alerted when an anomaly occurs. The type of anomaly can be different per case. A large class of anomalies relate to aberrations in an ADL routine of the person. For example, an above average number of toilet visits during the night. More severe incidents form another class, for example falls by the person. Further refined algorithms may also be needed when a (declining) trend in activity is to be detected.

By way of example, ADLs may include:
(i) Medication
 a. Is the elder taking his medicine in proper way at proper moments?
(ii) Sleep
 a. Is the elder sleeping sufficiently and undisturbed?
(iii) Eating/Drinking
 a. Is the elder eating sufficiently and regularly?
 b. Does he prepare meals by himself?
(iv) Physical activity
 a. Is the elder active during the day?
 b. Is there little sedentary behavior?
(v) Toileting
 a. Is the elder toileting in normal way?
 b. Are there frequent visits to the toilet during the night?
(vi) Bathing
 a. Is the elder bathing adequately?
(vii) Being In/Out House
 a. Is the elder going out?
(xiii) Ambient climate
 a. Is the environment "clean"?
 b. E.g., is temperature proper, is the $CO_2$ level healthy?
(ix) Etc.

Based on the above exemplary ADLs, the following examples warnings and alerts may be:
A. Sign of activity, or sign of inactivity
B. Presence in rooms considered risky (e.g. alone in kitchen when elder is suffering dementia)
C. Leaving the house at unexpected moments, such as during the night
D. Exceptional frequency or exceptional duration of toilet visits
E. Exceptional duration of bathing
F. Sleeping shorter
G. Reduced activity
H. Etc.

Embodiments of the present invention are therefore directed toward enabling ADLs of a person to be detected and/or monitored. This may be used to generate an alert signal for an alerting or warning system that can indicate the person is in need of help, for example.

Embodiments are based on the insight that control signals generated by an environment control system (such as a 'smart-home' control system for example) can be used to infer ADLs. Thus, instead of employing sensors and attempting to use the sensor data, proposed embodiment may obtain data (e.g. control data) directly from a control system and then analyze such data to determine ADL event of a person. By using data obtained directly from a control system, embodiments may determine (e.g. infer) information about an ADL of a person without relying on complex and/or expensive sensor arrangement, thus reducing costs. The installation, commission and maintenance of sensors in a monitoring environment may therefore be avoided by some embodiments.

Proposed is a concept of inferring ADLs of a person from usage data that is obtained from a control system used by the person to control one or more objects or devices. For example, a 'smart-home' control system may be adapted to control lighting and/or appliances within a monitored smart-home environment, and control signals generated by the smart-home control system may be analyzed so as to determine one or more ADLs of a person in the monitored smart-home environment. By way of example, lighting usage data may be obtained from lighting commands/signals generated by the control system, and such lighting usage data may be analyzed to infer an ADL of the person.

Embodiments thus propose the use of control/usage data from a control system (the control system being adapted controls one or more objects of a monitored environment according to a monitored person's requirements/instructions). Such a proposed ADL inference system/method may therefore be employed in a control system for controlling objects/items/devices within an environment.

Figure 1:
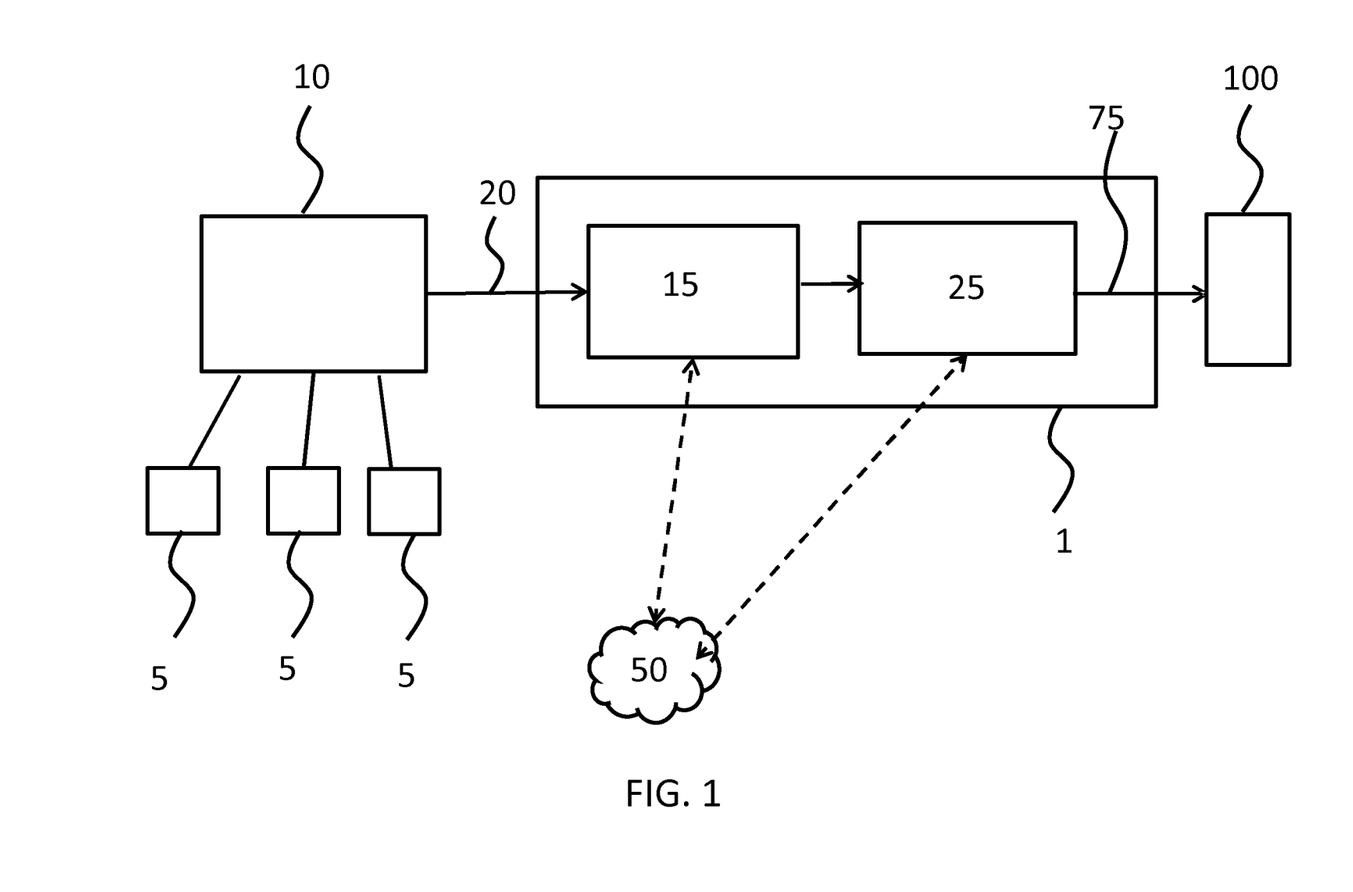
FIG. 1 is a simplified block diagram of a system for monitoring ADLs of a person within an environment according to an embodiment.

FIG. 1 shows an embodiment of a system 1 for monitoring ADLs of a person within an environment. In this example, the environment includes a plurality of lights 5 that may be controlled by the person via a lighting control system 10, wherein each of the plurality of lights 5 is positioned in a different room or area of the environment.

Here, the lighting control system 10 communicates control signals to the light 5 via wired or wireless connection. By way of example, the wireless connection may comprise a short-to-medium-range communication link. For the avoidance of doubt, short-to-medium-range communication link should be taken to mean a short-range or medium-range communication link having a range of up to around 100 meters. In short-range communication links designed for very short communication distances, signals typically travel from a few centimeters to several meters, whereas, in medium-range communication links designed for short to medium communication distances, signals typically travel up to 100 meters. Examples of short-range wireless communication links are ANT+, Bluetooth, Bluetooth low energy, IEEE 802.15.4, ISA100a, Infrared (IrDA), ISM Band, Near Field Communication (NFC), RFID, 6LoWPAN, UWB, Wireless HART, Wireless HD, Wireless USB, ZigBee. Examples of medium-range communication links include Wi-Fi, Z-Wave.

The lighting control system 10 is thus adapted to control each of the plurality of lights 5 according to instructions and/or requirements of the monitored person.

The system 1 comprises a data collection unit 15 adapted to obtain control data 20 from the lighting control system 10. Here, the control data 20 is based on one or more control signals generated by the lighting control system 10 for controlling the light 5. For instance, the control data 20 may comprise information relating to the parameters and/or properties of control signals issued to the lights 5 by the lighting control system 10. Such information about the parameters and/or properties may include, for example: timing of a control signal; the target/addressed light 5; a lighting parameter value (such as light brightness/luminosity, lighting color, dimming value, etc.); information about the control means (e.g. description of the items used by the user to provide the control signal, such as wireless button, smart-phone, motion sensor, etc.); rules programmed by the user; and originator of the signal (e.g. identification details of the person/user who caused the generation/issuance of the signal).

The system 1 further comprises a data analysis unit 25 adapted to determine an ADL event of the person based on the obtained control data 20. For this purpose, the data analysis unit 25 may communicate with one or more data processing resources available in the internet or "cloud" 50. Such data processing resources may undertake part or all of the processing required to infer or determine an ADL event of the person based on the obtained control data 20. Thus, the embodiment may employ distributed processing principles.

The data analysis unit 25 is further adapted to generate an output signal 75 representative of an inferred or determined ADL event of the monitored person. In other words, after determining an ADL event of the monitored person (based on the obtained control data from the lighting control system 10, either with or without communicating with data processing resources via the internet or "cloud"), an output signal 75 representative of a determined ADL event of the person is generated.

The system further comprises a graphical user interface (GUI) 100 for providing information to one or more users. The output signal 75 is provided to the GUI 100 via wired or wireless connection. By way of example, the wireless connection may comprise a short-to-medium-range communication link. As indicated in FIG. 1, the output signal 75 is provided to the GUI 100 from the data analysis unit 25. However, where the system, has made use of data processing resources via the internet or cloud 50, an output signal may be made available to the GUI 100 via the internet or cloud 50.

Based on the output signal 75, the GUI 100 is adapted to communicate information by displaying one or more graphical elements in a display area of the GUI 100. In this way, the system may communicate information about an ADL of the monitored person that may be useful for indicating that the person is in need of attention or for estimating when the person may be expected to require assistance or attention. For example, the GUI 100 may be used to display graphical elements to a medical practitioner, a caregiver, a family member or close relative. Alternatively, or in addition, the GUI 100 may be adapted to display graphical elements to the monitored person.

Thus, an ADL of the monitored person may be inferred from control data 20 (e.g. lighting usage data) that is obtained from lighting commands generated and issued by the lighting control system 10. Put another way, it is proposed to obtain and analyze data about the usage of lighting control (collected directly from a smart-home lighting control system). Since controllable lighting devices may be present in every room of a monitored environment, embodiments may be completely unobtrusive and no additional sensors and/or monitors (such a light switch monitors, or light sensors, etc.) may be required in order to determine and monitor an ADL. The monitored person need only undertake their normal activities when using the lighting control system 10 and may not even be aware that their usage of the lighting is being monitored.

Such use of control data from the lighting control system 10 may ensure that activity of the monitored person can be automatically and accurately obtained for all lighting usage without requiring the person to remember to undertake any special or additional activities in order for lighting usage to be detected. For example, it can remove the need for a person to perform a specific additional action (e.g. pressing a button) in order to indicate or log activity.

By way of example, the data analysis unit 25 may analyze the obtained control data 20 to detect an order or sequence of light activations and infer movement of the persons through the monitored environment (e.g. smart-home). From the inferred movement, one or more activities of the person may be deduced (e.g. visiting toilet, showering, etc.).

Further, on/off switching of (household) appliances or devices may be analyzed by the data analysis unit 25 so as to infer an activity of the person. The data analysis unit 25 may also recognize a repetitive user activity from the lighting and/or appliance usage (wake up and brushing teeth for example) and use this for coaching & long-term monitoring. For instance, a detected order of light activation/switching may be used to provide an indication of movement of the person through the environment (e.g. home) and deduce activities.

From the above description of the embodiment of FIG. 1, it will be understood that there is proposed a system which analyses device usage data from a control system so as to determine an ADL event of a monitored person. This may be thought of as providing an ADL detection and/or monitoring on a short term timescale (for example, at real-time). Such implementation may, for example, detect current ADLs and potentially identify recommended actions. For instance, if the monitored person determined to be in a so-called "risky room" for too long (as may be inferred from a toilet light being switched on longer than a predefined threshold time (e.g. 30 minutes or alternatively if twice as long as average of previous 5 times)), an alert signal may be provided to caregiver.

Other embodiments, however, may provide ADL detection and/or monitoring on a long term timescale (e.g. for pattern recognition and trend determination). Such implementation may, for example, obtain information about activities of the person, e.g. sleeping or eating. Also, deviations from usual patterns or trends may be detected and translated into an alert or alarm. Such deviations may relate to incidental deviations (e.g. user did not go to bed during the night) or indicate gradually increasing deviations (e.g. indication of cognitive decline, wandering, sleep disorder, confusion, vision degradation).

Thus, some embodiments may further comprise a monitor unit adapted to determine a trend in a capability or activity of the person based on a determined ADL event and historical data relating to previously determined ADL events of the person.

Accordingly, proposed is a concept for monitoring a person by determining a trend in the physical or mental capability of the person.

In general, to be able to observe trends in "normal" daily behavior of a person one may monitor ADLs of a person. From established trends, one may also spot unexpected activities, anomalies or deviations from expected values or patterns. The type of anomaly or irregularity can be different per case.

A large class of physical or mental capabilities can relate to an ADL routine of the person. For example, a physical capability may be inferred from the speed by which a person opens/closes a door (or a cupboard, wardrobe, fridge, microwave, or other furnishings) or a drawer and/or the force applied to the door or drawer during the opening/closing process. Another example is the brightness of lighting that is chosen for reading or a color shift due to degradation of the eye.

Embodiments of the present invention may therefore be directed toward enabling information about a physical or mental capability of a person to be obtained and potentially monitored. Such information may therefore be useful for monitoring the health or well-being of a person.

Some embodiments can employ a concept of determining a trend in a (physical or mental) capability or activity of a person from a currently inferred or determined ADL of the person and historical data relating to one or more previously detected ADLs of the person. In other words, determination of a trend in a capability or activity of a person may be based on current and previously detected ADLs of the person.

A trend in a (physical or mental) capability or activity of a person may therefore be determined without requiring sensors to be installed in the monitored environment, thus reducing the cost and/or complexity of a system according to an embodiment. It may also help to ensure anomalies are accurately detected, thus improving the accuracy of ADL monitoring results. Such a proposed concept for monitoring a physical or mental capability or activity of a person may therefore be employed in a system for monitoring ADLs of a person within an environment.

For the purpose of such long-term monitoring and/or trend identification, determined ADL events (and associated values) may be stored in a database adapted to store historical data relating to one or more previously detected ADLs. In doing so, each ADL event may be labelled with the timestamp identifying when the ADL event was measured. In the trend determination or analysis, the detected values may then be averaged per time unit, e.g. per day, before the trend is estimated. Also, given a (known) context, one may also exclude certain days. For example, on Fridays, the grandchildren or a cleaning lady are in the house and so detected data may not be representative of the monitored person.

Another approach may be to provide each detected ADL event as a pair of time and value, so that trend analysis, using a regression method for example, may account for the varying rate (e.g. irregularity in arrival) at which values are detected.

By storing previous detected ADLs, estimates of a trend in the ADLs may be determined and a future date/time at which the person may require help or assistance may be identified (e.g. by extrapolating the trend to identify when it goes above/below a threshold value). Furthermore, currently detected ADLs may be used to re-calculate or refine previously determined trends (e.g. those stored in a database for example). Further, embodiments may be self-learning (e.g. using machine learning algorithms) by using previously detected ADLs. For example, an embodiment may detect that certain conditions/events (e.g. accident) occur after certain data/event conditions, and may learn from this to predict the occurrence of the same or similar events for other users (and thus potentially cause the issuance of a warning signal in attempt to prevent the occurrence).

Although the embodiment of FIG. 1 described employs lighting usage data from a lighting control system used by a monitored person, it will be understood that many other different types of usage data derived from a control system may be obtained and analyzed in alternative embodiments. For example, other embodiments may be arranged to obtain and analyze: heating control/usage data; electrical appliance control/usage data; and/or door entry control/usage data.

By detecting ADLs based on usage/control data relating to objects that the person interacts with, a trend in the detected ADLs over time may be identified and, from such a trend, a capability or activity of a person may be monitored. For example, a trend of slowing/increasing reaction time of the person controlling a device (as detected directly from control signals of the control system) may be used to identify and monitor a trend in the person's cognitive abilities.

Figure 2:
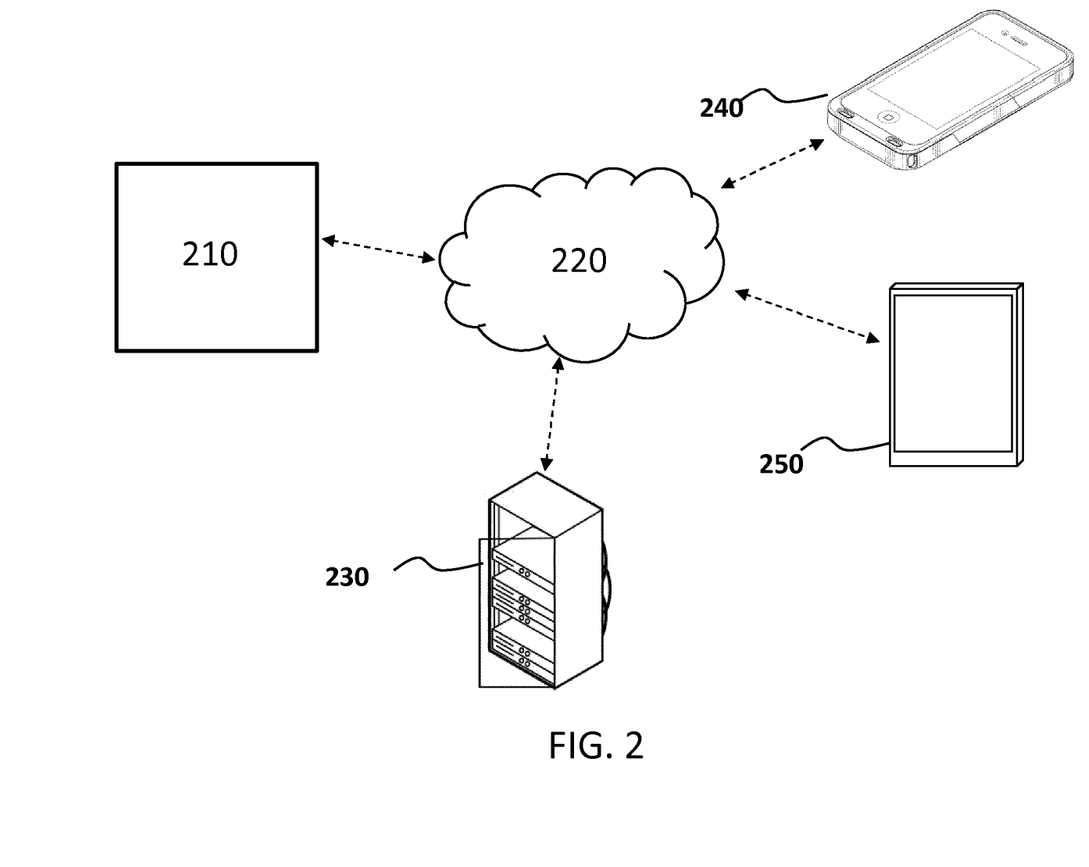
FIG. 2 is a simplified block diagram of a system for monitoring ADLs of a person within an environment according to another embodiment.

Referring now to FIG. 2, there is depicted another embodiment of a system according to the invention comprising a control system 210 adapted to control a plurality of devices and/or appliances present in a monitored environment. Here, the control system 210 comprises a smart-home control system which is adapted to be provided in the monitored environment and controlled by a person to be monitored. The control system 210 is adapted to output one or more control signals which are adapted to control the devices/appliances of the monitored environment based on instructions and/or requirements of the monitored person.

Although this embodiment has been described as integrating the control system 210 into the monitored environment, it will be understood that, in alternative embodiments, the control system 210 may be provided separately from the monitored environment such that it is remotely provisioned and communicates control signals to the monitored environment (e.g. via the internet or a wireless communication link).

The control system 210 is adapted to communicate control information about generated control signals (e.g. copies of the control signals or control data comprising information relating to parameter values of the control signals) via the internet 220 (using a wired or wireless connection for example) to a remotely located data processing system 230 (such as server).

The data processing system 230 is adapted to receive the control information from the control system 210 and process the received information in accordance with an inference/detection algorithm in order to infer/determine a trend in an ADL of the person. More specifically, the algorithm processes the received information from the control system 210 in combination with historical data relating to one or more previously detected ADLs of the person to determine a trend in the ADL over time. The trend can be found as a linear line (e.g., using linear regression), but may also be curved using higher order fitting techniques.

The data processing system 230 is further adapted to generate output signals representative of inferred or calculated ADL trend. Thus, the data processing system 230 provides a centrally accessible processing resource that can receive information from the control system 210 and run one or more algorithms to transform the received information into a description of a trend in an ADL of the person.

Previously determined ADLs (or values of a property of the ADLs) may therefore be stored, in a historical database for example, and then used in subsequent calculations. Furthermore, currently detected ADLs or values may be used to re-calculate or refine a previously determined trend. Thus, the behavioral pattern of activities of the person may be stored. Shifts in this pattern may indicate that the person is in need of help. For example, the person may start forgetting to take a regular shower, and this may be inferred from a trend in a frequency of command signals issued to a shower room of the monitored home by the control system of the home.

Further, the data processing system 230 is adapted to detect an irregularity in the historical database. For example, by adding time information to the determined ADL(s), the time spent between the activities may be determined. With the time information, the frequency of the activity may be determined. For example, the frequency of the determined activity 'preparing a hot meal' may be 'once a day', or '5 times a week'. An irregularity in the historical database may then, for example, be that the time spent between the determined activities of 'preparing a hot meal' has increased.

Such provision of information about a detected or inferred ADL trend and/or irregularity may be undertaken in response to a receiving a request (via the internet 220 for example) and/or may be undertaken without request (i.e. 'pushed').

For the purpose of receiving information about a detected or inferred ADL trend from the data processing system, and thus to enable the person to be monitored, the system further comprises first 240 and second 250 mobile computing devices.

Here, the first mobile computing device 240 is a mobile telephone device (such as a smartphone) with a display for displaying graphical elements representative of a person's physical or mental well-being. The second mobile computing device 250 is a mobile computer such as a Laptop or Tablet computer with a display for displaying graphical elements representative of a person's ADLs.

The data processing system 230 is adapted to communicate output signals to the first 240 and second 250 mobile computing devices via the internet 220 (using a wired or wireless connection for example). As mentioned above, this may be undertaken in response to receiving a request from the first 240 or second 250 mobile computing devices.

Based on the received output signals, the first 240 and second 250 mobile computing devices are adapted to display one or more graphical elements in a display area provided by their respective display. For this purpose, the first 240 and second 250 mobile computing devices each comprise a software application for processing, decrypting and/or interpreting received output signals in order to determine how to display graphical elements. Thus, the first 240 and second 250 mobile computing devices each comprise a processing arrangement adapted to one or more values representative of a trend, and to generate a display control signal for modifying at least one of the size, shape, position, orientation, pulsation or color of the graphical element based on the one or more values representative of trend.

The system can therefore communicate information about an inferred or detected ADL trend to users of the first 240 and second 250 mobile computing devices. For example, each of the first 240 and second 250 mobile computing devices may be used to display graphical elements to a medical practitioner, a caregiver, a family member or close relative. Also, the system can generate a warning signal in response to a detected irregularity. The irregularity may, for example, indicate that the person is in need of help and thus a generated alert or warning signal may be provided to at least one of: the person; a medical practitioner; and a caregiver.

Implementations of the system of FIG. 2 may vary between: (i) a situation where the data processing system 230 communicates display-ready ADL trend data, which may for example comprise display data including graphical elements (e.g. in JPEG or other image formats) that are simply displayed to a user of a mobile computing device using conventional image or webpage display (which can be web based browser etc.); to (ii) a situation where the data processing system 230 communicates raw data set information that the receiving mobile computing device then processes to determine a trend in an ADL, and then displays graphical elements based on the determined trend (for example, using local software running on the mobile computing device). Of course, in other implementations, the processing may be shared between the data processing system 230 and a receiving mobile computing device such that part of the data generated at data processing system 230 is sent to the mobile computing device for further processing by local dedicated software of the mobile computing device. Embodiments may therefore employ server-side processing, client-side processing, or any combination thereof.

Further, where the data processing system 230 does not 'push' information (e.g. output signals), but rather communicates information in response to receiving a request, the user of a device making such a request may be required to confirm or authenticate their identity and/or security credentials in order for the information to be communicated.

Figure 3:
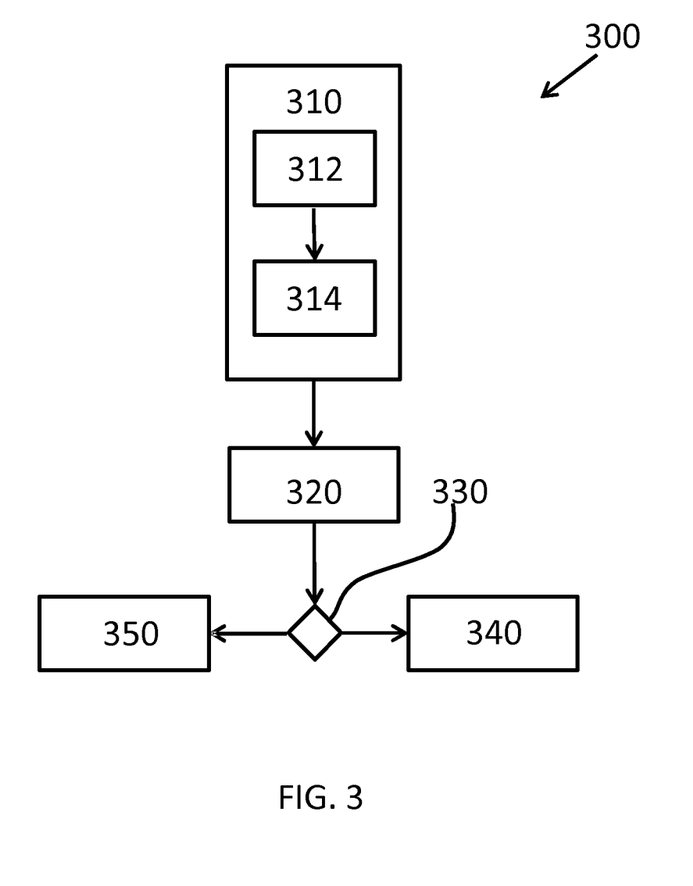
FIG. 3 is a flow diagram of a method for monitoring ADLs of a person within an environment according to an embodiment.

Referring now to FIG. 3, there is shown a flow diagram of an exemplary method 300 for monitoring ADLs of a person within an environment. Here, the environment contains a plurality of devices that may be controlled via a centralized control system.

The method begins with step 310 in which an ADL event of the person is detected. Specifically, the step 310 of detecting an ADL event comprises the sub-steps of: obtaining 312 control data from the control system, the control data being based on one or more control signals generated by the control system for controlling the devices; and determining 314 an ADL event of the person based on the obtained control data.

Next, in step 320, a trend in a capability or activity of the person is determined based on the detected ADL that was detected in step 314 and historical data relating to one or more previously detected ADLs (caused by the monitored person).

Then, in step 330, the determined trend is compared with a predetermined threshold value. The threshold value can be preprogrammed, fixed or dynamically set in response to calculations based on one or more previously obtained ADLs (e.g. using trend analysis), but is preferably also enabled to be set by a user preference. Thus, the threshold may be based on previously determined values representative of a physical or mental capability the person. In other words, the threshold may be defined by taking account of a history of the person and/or taking account of previous calculations so that it can be used to identify outlying values or anomalies.

If, in step 330, the trend is determined to exceed the first threshold value, the method proceeds to step 340 wherein a warning signal is generated and output along with information describing the trend and/or the detected ADL/value. If, in step 330, the trend is determined to not exceed the first threshold value, the method proceeds to step 350 wherein the information describing the trend and/or the detected value of rotational velocity of the fridge door is output without any warning signal.

From the above description of the method illustrated by FIG. 3, it will be understood that proposed embodiments may be adapted to detect an irregularity in a determined trend. For example, in the embodiment of FIG. 3, the steps of 330 to 350 may be implemented by a monitor unit and be implemented to detect an irregularity based on a comparison of a determined trend with a threshold value. This may provide the advantage that an alarm or alert signal may be generated and communicated when an irregularity or anomaly is detected (e.g. if the person stays too long in the bathroom with the hot shower running, indicating that the person may have become unwell in the bathroom). In this example, to detect an irregularity, the monitor unit undertakes a relatively simple comparison of the determined trend with a threshold value. The threshold may be preprogramed and fixed, but it may be preferable to enable the threshold value to be set by a user preference. This may identify when a threshold value may be exceeded in the future, for example.

Other methods to detect outliers or to detect changes in a time series are known in the art. By way of example, in an embodiment, the monitor unit may be further adapted to calculate an estimated future value of the property based on the determined trend, and the monitor unit may be further arranged to detect an irregularity based on a comparison of the estimated future value of the property with a threshold value and to generate an alert output signal in response to the detected irregularity. A threshold value may thus relate to a future value, and a determined trend may be extrapolated for comparison of an extrapolated value with the future threshold value. Using the extrapolated trend, one may estimate the time until the trend will cross the threshold, and provide that number as an identification of when intervention or assistance may be required, for example.

Purely by way of example, one or more steps of the method 300 for monitoring a physical or mental capability of a person may be implemented in a portable computing device (such as the smartphone or portable computer shown in FIG. 2) in order to control the display of graphical elements on a display. Of course, it will be understood that proposed embodiments for monitoring an ADL may be implemented in other methods and/or systems.

Embodiments may further comprise a control unit adapted to generate one or more control signals for the control system based on the determined ADL event. In this way, embodiments may be adapted to provide control signals that are suitable for use by the control system from which the control/usage data has been obtained. Such embodiments may therefore modify or control operation of the control system (and thus the object(s) controlled by the control system). In this way, the operation of the control system may be arranged to be responsive to (or dependent upon) detected ADLs of the person.

Accordingly, rather than just monitoring usage of a control system, some embodiments may be adapted to operate the control system so as treat/influence the person and improve his/her well-being. For example, if reading activity is detected, and if it happens continuously in low light, an embodiment may communicate a control signal to the control system which causes the control system to change or improve the lighting conditions.

It is also noted that, although it has been described above that embodiments need not employ sensors, some embodiments may further comprise a sensor adapted to detect a value of a property of at least one of: the environment, control/operation of the object, and the object; and to generate a sensor output signal representative of the detected value. Such a sensor arrangement may help to improve the accuracy of ADL determination for example. Sensor readings may, for instance, qualify or refine data analysis undertaken by the data analysis unit.

The sensor(s) may be arranged in a strategic location/position so as to detect an appropriate value without the person needing to intentionally or consciously activate/operate the sensor. In this way, a person may only need to undertake their normal activities. Such strategic positioning may ensure that a value of a property of the person or environment can be automatically and accurately obtained, and this may not require the person to remember to undertake any special or additional activities in order for a value to be detected by the sensor. This may remove the risk of the person forgetting to activate a sensor (e.g. by pressing a button), for example.

There exist many sensors that can be employed by embodiments. A sensor may be adapted to sense control of the object for example. Other sensors may be adapted to sense a person for example.

Typical sensors include PIR (Passive Infra-Red; measure movement and presence), OC (open-close; measure state of doors, in particular front doors, windows, and cupboards, including refrigerators), power sensors (measure current consumption of appliances, such as microwave, water cookers, TV, etc.), and pressure mats (measure occupancy of user sitting in chair, lying in bed, standing on door mat in front of front door, etc.). Many others exist and are conceivable, such as sensors to sense light switch state, or sensors that measure environmental conditions such as humidity, $CO_2$ level (or CO and smoke), etc. A further range of sensors are those based on physical quantities, such as accelerometers, magnetometers, gyroscopes, and air pressure sensors. Accelerometers, for example, can also measure state of doors and their open-close movements. Yet another range of sensors consists of microphones and cameras (including infra-red (IR), or even UV and beyond, part of spectrum), to which also belong GPS and location-sensitive IR. Ultra-sound or RF-based sensors, including RFID tagging, provide additional input. Appliances having an own IP-address, known as the internet-of-things, provide further sensor input signals that can be taken by the smart-home control system.

Although the sensor(s) may be mounted in the environment (e.g. the person's home), they may also be attached to user utilities (such as a keyring) or put in clothes, in a pocket or bag, or as insole or undergarment, etc. They may also be fabricated to be worn explicitly like a wrist watch or pendant. Further, the sensors may communicate their output signals via a wired or wireless connection, or a combination thereof.

The sensors may also be adapted to undertake primary processing of the detected values, such a signal filtering, sampling, conditioning, etc., so as to reduce a required transmission bandwidth and/or transmission duration for example.

Non-intrusive monitoring may therefore be realized with relative simple sensors that provide data on specific ambient conditions or properties/parameters of the environment (such as temperature or humidity for example), or properties of the person (such as movement, for example). Such sensors for measuring ambient conditions or properties/ parameters of the environment may be simple, small and/or cheap. Also, the movement of the person may be detected with, for example, a Passive InfraRed (PIR) sensor which is a cheap component. Movement sensors may be used to switch on lighting and people are therefore typically familiar with their usage. Thus, embodiments may employ sensors that are considered to be non-intrusive and more easily accepted by the monitored person. Yet, with the data provided by these sensors, ADLs may be more accurately determined and provide more information on the person being monitored.

For example, with a humidity sensor and a movement sensor in the bathroom it may be inferred that the person is taking a shower. In a further example, with a temperature sensor and a movement sensor in the kitchen it may be determined that the person is preparing a hot meal. It is a further advantage that the sensors may be stationary sensors that are located for example in the bathroom and in the kitchen, thus making it unnecessary for the person to wear a device.

Thus, some embodiments of the invention may employ conventional sensors and/or existing sensor arrangements. Also, embodiments may employ sensors that are considered to be non-intrusive and more easily accepted by the monitored person.

Such sensors may be employed by, or in conjunction with, embodiments so as to increase the number and/or accuracy of monitored ADLs. They may also be used to confirm or qualify analysis that has been undertaken on usage data obtained from a control system, so that spurious or unintentional determinations/inferences are avoided. For example, signals from a location sensor worn by the monitored person may be used to confirm if lighting system commands are indeed attributable to the monitored person or some other person, for example. It can be noted that connected lighting system and smart home systems already increasingly comprise sensors, purely for their own enhanced functionality. These sensors can be used for the purpose of this invention (e.g. an existing/conventional motion sensor).

Figure 4:
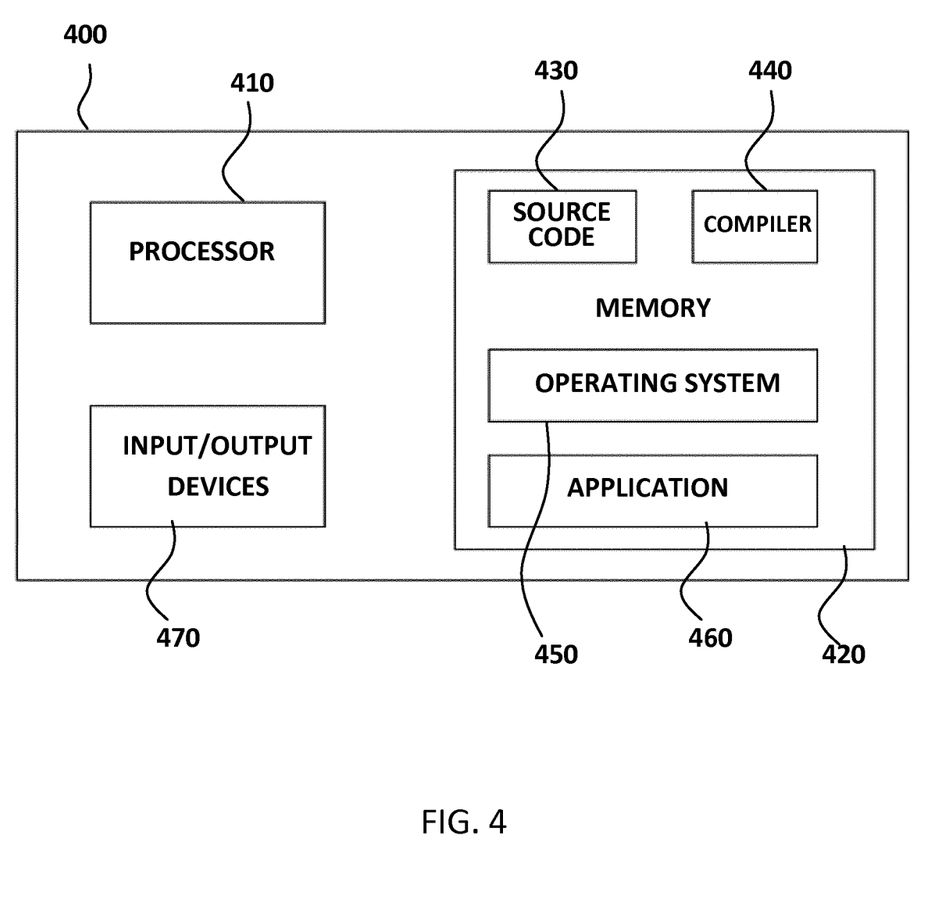
FIG. 4 is a simplified block diagram of a computer within which one or more parts of an embodiment may be employed.

FIG. 4 illustrates an example of a computer 400 within which one or more parts of an embodiment may be employed. Various operations discussed above may utilize the capabilities of the computer 400. For example, one or more parts of an ADL monitoring system adapted to monitor a person may be incorporated in any element, module, application, and/or component discussed herein.

The computer 400 includes, but is not limited to, PCs, workstations, laptops, PDAs, palm devices, servers, storages, and the like. Generally, in terms of hardware architecture, the computer 400 may include one or more processors 410, memory 420, and one or more I/O devices 470 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 410 is a hardware device for executing software that can be stored in the memory 420. The processor 410 can be virtually any custom made or commercially available processor, a central processing unit (CPU), a digital signal processor (DSP), or an auxiliary processor among several processors associated with the computer 400, and the processor 410 may be a semiconductor based microprocessor (in the form of a microchip) or a microprocessor.

The memory 420 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 420 may incorporate electronic, magnetic, optical, and/or other types of storage media. Note that the memory 420 can have a distributed architecture, where various components are situated remote from one another, but can be accessed by the processor 410.

The software in the memory 420 may include one or more separate programs, each of which comprises an ordered listing of executable instructions for implementing logical functions. The software in the memory 420 includes a suitable operating system (O/S) 450, compiler 440, source code 430, and one or more applications 460 in accordance with exemplary embodiments. As illustrated, the application 460 comprises numerous functional components for implementing the features and operations of the exemplary embodiments. The application 460 of the computer 400 may represent various applications, computational units, logic, functional units, processes, operations, virtual entities, and/or modules in accordance with exemplary embodiments, but the application 460 is not meant to be a limitation.

The operating system 450 controls the execution of other computer programs, and provides scheduling, input-output control, file and data management, memory management, and communication control and related services. It is contemplated by the inventors that the application 460 for implementing exemplary embodiments may be applicable on all commercially available operating systems.

Application 460 may be a source program, executable program (object code), script, or any other entity comprising a set of instructions to be performed. When a source program, then the program is usually translated via a compiler (such as the compiler 440), assembler, interpreter, or the like, which may or may not be included within the memory 420, so as to operate properly in connection with the O/S 450. Furthermore, the application 460 can be written as an object oriented programming language, which has classes of data and methods, or a procedure programming language, which has routines, subroutines, and/or functions, for example but not limited to, C, C++, C#, Pascal, BASIC, API calls, HTML, XHTML, XML, ASP scripts, FORTRAN, COBOL, Perl, Java, ADA, .NET, and the like.

The I/O devices 470 may include input devices such as, for example but not limited to, a mouse, keyboard, scanner, microphone, camera, etc. Furthermore, the I/O devices 470 may also include output devices, for example but not limited to a printer, display, etc. Finally, the I/O devices 470 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 470 also include components for communicating over various networks, such as the Internet or intranet.

If the computer 400 is a PC, workstation, intelligent device or the like, the software in the memory 420 may further include a basic input output system (BIOS) (omitted for simplicity). The BIOS is a set of essential software routines that initialize and test hardware at startup, start the O/S 450, and support the transfer of data among the hardware devices. The BIOS is stored in some type of read-only-memory, such as ROM, PROM, EPROM, EEPROM or the like, so that the BIOS can be executed when the computer 400 is activated.

When the computer 400 is in operation, the processor 410 is configured to execute software stored within the memory 420, to communicate data to and from the memory 420, and to generally control operations of the computer 400 pursuant to the software. The application 460 and the O/S 450 are read, in whole or in part, by the processor 410, perhaps buffered within the processor 410, and then executed.

When the application 460 is implemented in software it should be noted that the application 460 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

The application 460 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

From the above description, it will be appreciated that embodiments propose to use an environment control system (such as a lighting system for example) for the purposes of detecting and monitoring ADLs of a person. Embodiments may therefore be useful for monitoring of elderly, disabled or unwell individuals so to support independent living. Usage data from the control system can be used both for real-time ADL detection and alerts, as well as to detect gradual deviations from usual patterns or trends.

Embodiments may be supported by the current and future trends towards smart-homes or connected lighting.

The description has been presented for purposes of illustration and description, and is not intended to be exhaustive or limited to the invention in the form disclosed. Many modifications and variations will be apparent to those of ordinary skill in the art. Embodiments have been chosen and described in order to best explain principles of proposed embodiments, practical application(s), and to enable others of ordinary skill in the art to understand that various embodiments with various modifications are contemplated.

The invention claimed is:

1. A system for monitoring activities of daily living, ADLs, of a person within an environment, the environment containing an object, the object comprising a light or home appliance adapted to be used for an execution of the ADL, the object being controllable by the person via a control system, the system comprising:
   a data collection unit adapted to obtain control system usage data directly from control data from the control system, the control data being based on one or more control signals generated by the control system to control the object; and
   a data analysis unit adapted to determine an ADL event of the person based on the obtained control system usage data,
   wherein the control system is a lighting or smart home control system and the control system usage data comprises lighting usage data obtained from lighting commands generated and issued by the control system.

2. The system of claim 1, further comprising:
   a monitor unit adapted to determine a trend in a capability or activity of the person based on the determined ADL event and historical data relating to previously determined ADL events of the person.

3. The system of claim 2, wherein the monitor unit is further adapted to detect an irregularity in the determined trend, and wherein the monitor unit is further arranged to generate an alert signal in response to the detected irregularity.

4. The system of claim 3, wherein the monitor unit is adapted to detect an irregularity based on a comparison of the determined trend with a threshold value.

5. The system of claim 4, wherein the threshold value is determined based on at least one of:
   one or more previously determined ADL events of the person; and one or more previously determined changes in ADL events of the person.

6. The system of claim 1, wherein the data analysis unit is further adapted to store the determined ADL of the person in an activity database, and wherein the data analysis unit is further adapted to detect an irregularity in the activity database and to generate a warning signal in response to the detected irregularity.

7. The system of claim 6, wherein the data analysis unit is further adapted to determine a frequency of an ADL in the activity database, the detected irregularity being dependent on a change in the frequency.

8. The system of claim 1, further comprising:
a sensor adapted to detect a value of a property of at least one of: the environment and the object; and to generate a sensor output signal representative of the detected value,
and wherein the data analysis unit is adapted to determine the ADL event of the person further based on the detected value.

9. The system of claim 1, further comprising:
a control unit adapted to generate a control signal for controlling the object based on the determined ADL event.

10. The system of claim 1, further adapted to generate a display control signal for modifying a graphical element based on the determined ADL event of the person,
and wherein the system further comprises:
a display system adapted to display the graphical element in accordance with the generate display control signal.

11. The system of claim 1, wherein the determined ADL of the person is taken from a group comprising: eating; cooking; medicating; sleeping; toileting; bathing; and washing.

12. A method for monitoring activities of daily living, ADLs, of a person within an environment, the environment containing an object, the object comprising a light or home appliance adapted to be used for an execution of the ADL, the object being controllable by the person via a control system, the method comprising:
obtaining control system usage data directly from control data from the control system, the control data being based on one or more control signals generated by the control system to control the object; and
determining an ADL event of the person based on the obtained control system usage data,
wherein the control system is a lighting or smart home control system and the control system usage data comprises lighting usage data obtained from lighting commands generated and issued by the control system.

13. The method of claim 12, further comprising:
determining a trend in a capability or activity of the person based on the determined ADL event and historical data relating to previously determined ADL events of the person.

14. A non-transitory computer readable storage medium comprising a computer program product for monitoring activities of daily living, ADLs, of a person within an environment, the environment containing an object controllable by the person via a control system, wherein the computer program product comprises computer-readable program code configured to perform all of the steps of claim 12 when executed on one or more processors.

* * * * *